(12) United States Patent
Mish et al.

(10) Patent No.: US 9,855,448 B2
(45) Date of Patent: *Jan. 2, 2018

(54) SUN-CARE COMPOSITIONS

(76) Inventors: James Mish, Newtown, PA (US); Hani M. Fares, Somerset, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/500,540

(22) PCT Filed: Oct. 4, 2010

(86) PCT No.: PCT/US2010/051268
§ 371 (c)(1),
(2), (4) Date: Jun. 1, 2012

(87) PCT Pub. No.: WO2011/044015
PCT Pub. Date: Apr. 14, 2011

(65) Prior Publication Data
US 2012/0230931 A1   Sep. 13, 2012

Related U.S. Application Data

(60) Provisional application No. 61/250,268, filed on Oct. 9, 2009.

(51) Int. Cl.
*A61K 8/49* (2006.01)
*A61Q 17/04* (2006.01)
*A61K 8/81* (2006.01)

(52) U.S. Cl.
CPC ............ *A61Q 17/04* (2013.01); *A61K 8/4966* (2013.01); *A61K 8/8158* (2013.01)

(58) Field of Classification Search
None
See application file for complete search history.

(56) References Cited

U.S. PATENT DOCUMENTS

| | | | |
|---|---|---|---|
| 5,204,090 A * | 4/1993 | Han | 424/59 |
| 6,060,547 A * | 5/2000 | Canter et al. | 524/280 |
| 7,309,682 B2 * | 12/2007 | Lupia et al. | 510/119 |
| 2006/0188458 A1 | 8/2006 | Traynor et al. | |
| 2009/0035234 A1 * | 2/2009 | Cunningham et al. | 424/59 |
| 2009/0035243 A1 * | 2/2009 | Czarnota et al. | 424/64 |

FOREIGN PATENT DOCUMENTS

WO   WO 2008/080892   7/2008

OTHER PUBLICATIONS

Couteau, Pharmazie, 62, 2007.*

* cited by examiner

*Primary Examiner* — Robert A Wax
*Assistant Examiner* — William Craigo
(74) *Attorney, Agent, or Firm* — Thompson Hine LLP; William J. Davis

(57) ABSTRACT

A sun-care composition having an SPF value of at least 15 comprising: (a) one or more sun care actives including a ów-resorcinyl triazine compound; (b) an acrylates/octylacrylamide copolymer; and (c) a pharmaceutically/cosmetically/dermatologically acceptable vehicle.

12 Claims, 1 Drawing Sheet

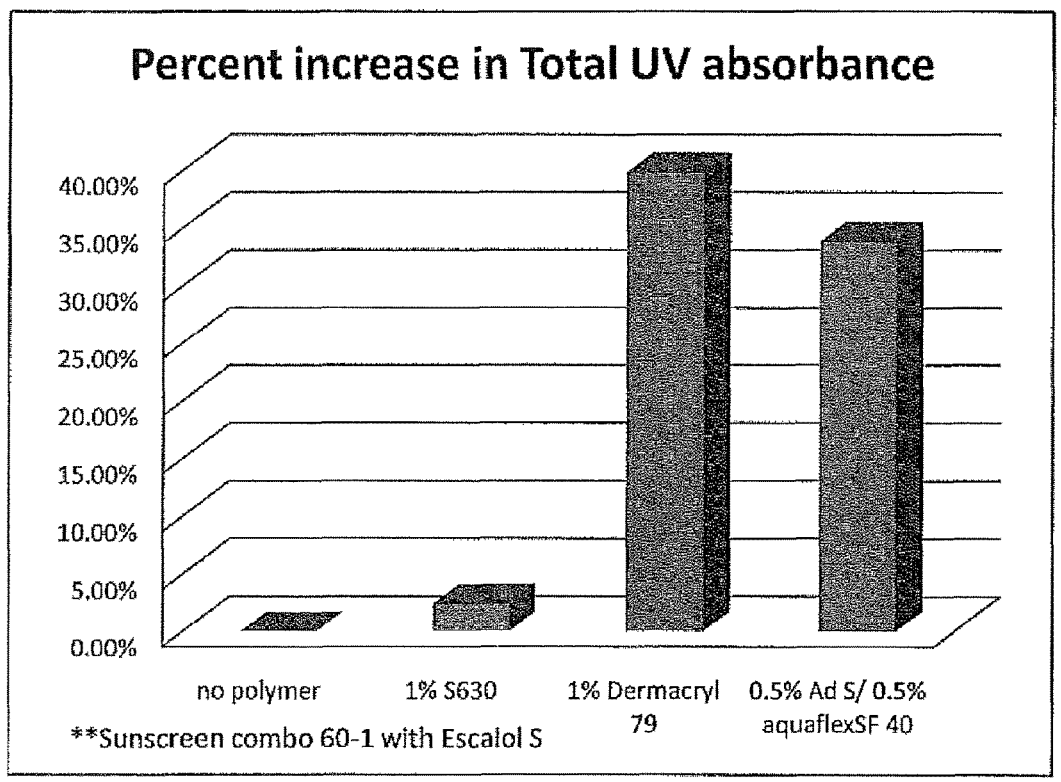
*0. 5% Advantage S/0. 5% AquaFlex SF-40

SUN-CARE COMPOSITIONS

BACKGROUND OF THE INVENTION

Technical Field of the Invention

The present invention relates to a sun-care composition having an SPF value of at least 15 comprising: (a) one or more sun care actives including a bis-resorcinyl triazine compound; (b) an acrylates/octylacrylamide copolymer; and (c) a cosmetically/dermatologically acceptable vehicle. The sun-care actives include UV-A and/or UV-B sunscreens or mixtures thereof.

More particularly, the present invention relates to sunscreen compositions that provide a boost in the SPF value of the composition and provide enhanced sensory properties when applied. Thus, the present invention provides compositions that provide efficient photo protection and that can be applied in a smooth, continuous film over the skin which leaves the skin feeling soft and silky.

Description of the Prior Art

UV radiation is part of the electromagnetic (light) spectrum that reaches the earth from the sun. It has wavelengths shorter than visible light, making it invisible to the naked eye. These wavelengths are classified as UVA, UVB, or UVC, with UVA the longest of the three at 320-400 nanometers (nm, or billionths of a meter). UVB ranges from 290 to 320 nm. With even shorter rays, most UVC is absorbed by the ozone layer and does not reach the earth.

Sunlight or ultraviolet radiation in the UV-B range is known to be the primary cause of sunburn whereas UV-A radiation, which makes up 90% of solar radiation produces tanning of the skin. However, in that process, UV-A rays cause, in particular, a loss in the elasticity of the skin and the appearance of wrinkles, promoting a premature aging thereof.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

Sunscreen compositions are applied to the skin to protect the skin from the sun's ultraviolet rays. Over the past 10 years, awareness of the detrimental effects of unprotected UV exposure has increased and, as a result, consumers are seeking higher levels of protection. Further the standards of the sunscreens have been raised by stringent testing requirement by Regulatory authorities. The most significant changes within these regulations are the new requirements for UVA protection and the added test for photostability of finished sunscreen formulations. The majority of sun care products currently require SPF levels of at least 30, reaching upwards of 50+. As a result, high levels of UVA protection are required in order to make a UVA claim.

As the sun-care market is becoming more competitive, companies are separating themselves from competitors by launching higher SPF products and thus claiming higher UV protection. To achieve protection across a wide range, sunscreen makers may include several different sunscreen ingredients. One of the most opted way of achieving higher SPF values, is to increase the amount of sunscreens in the product. This approach however will increase the cost of the product and might negatively impact the sensory characteristics of the product. Others have added small amounts of UV absorbers like butyl octyl salicylate as boosters to formulations. Others increased SPF by adding light scattering/refracting polymers to the product such as styrene/acrylates copolymers.

Among the most desirable options is finding a number of absorbers that work in synergy or by using various polymers that provide a continuous film on the skin. A wide variety of cosmetic/dermatological compositions intended for the enhanced performance of sun-screens of human skin is known in the art.

U.S. Pat. No. 7,368,105 discloses photoprotective composition comprising at least one dibenzoylmethane UV-screening agent a stabilizing admixture comprising arylalkyl benzoate compound and at least one bis-resorcinyl triazine compound.

U.S. Pat. No. 6,916,464 describes a sunscreen gel composition in Example 2 containing 2% Dermacryl 79. However, the composition exhibited relatively low SPF and did not contain a bis-resorcinyl triazine sunscreen agent.

A consumer consideration while purchasing a sunscreen product is how the product feels and how well it spreads over the skin. Typically, consumers want a sunscreen that feels soft and silky and can be applied in a smooth, continuous film over the skin. Ultimately, product feel could determine whether the consumer decides to purchase the product.

With such an advancement and awareness among the consumer, it is always and foremost desired to have sunscreens formulated with the goal of inhibiting skin damage from the sun's rays. The sunscreen composition filters or blocks the harmful UV-A and UV-B rays that can damage and harm the skin. Thus, it is the primary objective of the present invention to provide sun-care compositions with enhanced performance and aesthetics.

SUMMARY OF THE INVENTION

We have discovered that sun-care compositions comprising one or more sun-care actives including a bis-resorcinyl triazine compound in combination with specific acrylates/octylacrylamide copolymers exhibit enhanced/elevated efficiency of the sun-screen active. The compositions of the invention provide the user with an enhanced soft, silky feel when applied to skin while still providing superior protection from damaging ultraviolet light.

In accordance with the present invention, there is provided a sun-care composition comprising one or more sun-care actives including a bis-resorcinyl triazine compound in combination with specific acrylates/octylacrylamide copolymers which are capable of enhancing/elevating the efficiency of the sun-screen.

More specifically, the present invention provides a sun-care composition having an SPF value of at least 15 comprising:
  (a) one or more sun care actives including a bis-resorcinyl triazine compound;
  (b) an acrylates/octylacrylamide copolymer; and
  (c) a pharmaceutically/cosmetically/dermatologically acceptable vehicle.

The sun-care active can be selected from the group consisting of UV-A, UV-B, physical sun blockers and combinations thereof. The sun-care composition of the present invention has an SPF of at least about 25, preferably from about 50 to about 130.

This invention also provides a method for enhancing the SPF-value of one or more sun-care agents in UV-photoprotecting sun-care compositions comprising admixing and intimately formulating the pharmaceutically/cosmetically/ dermatologically acceptable carrier and an acrylates/octylacrylamide copolymer in an amount effective to enhance the SPF value of said one or more sun-care actives including a bis-resorcinyl triazine compound.

DETAILED DESCRIPTION OF PREFERRED EMBODIMENTS

The present invention relates to a SPF enhanced sun-care composition comprising one or more sun-care actives including a bis-resorcinyl triazine compound, an acrylates/octylacrylamide copolymer and a pharmaceutically/cosmetically/dermatologically acceptable vehicle.

While applicants do not wish to be bound by any theories, it is believed that the mechanism of enhancement of SPF is generally attributed to the ability of the polymer to make a uniform film of the product onto the skin. The distribution of the sunscreen actives in the film is considered key to the boosting effect of such polymer. In addition, the uniformity of the film is also of great importance. Since the surface of the skin is really not very uniform, many polymers do not have the ability of forming continuous films on the skin. That is why not all film formers are considered SPF boosters. The ability to identify such classes of polymers is of key value to formulation chemists as it allows them to achieve higher SPF values with less sunscreen in their formulations. Thus, spreadability, dispersability, uniformity, solubility and compatibility of the selective film polymers as described in the present invention leads to the elevated SPF of the sunscreens desired by the present day customers.

The sunscreen composition of the present invention is uniquely formulated to provide an elevated SPF and enhanced feeling of softness and silkiness when the sunscreen composition is applied to the skin. Moreover, the composition is capable of being easily and uniformly applied over the skin. These enhanced properties are achieved, in large part, by formulating the sunscreen composition as described herein.

The bis-resorcinyl triazine compounds in accordance with the present invention correspond to formula (I) below:

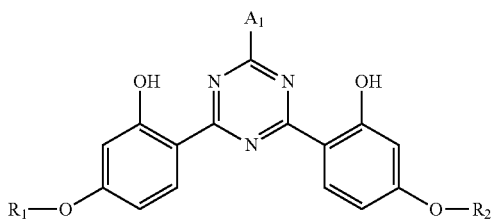

(1)

in which: (i) the radicals $R_1$ and $R_2$, which may be identical or different, are each a $C_3$-$C_{18}$ alkyl radical, a $C_2$-$C_{18}$ alkenyl radical or a residue of formula —$CH_2$—CH(OH)—$CH_2$—$OT_1$, in which $T_1$ is a hydrogen atom or a $C_1$-$C_8$ alkyl radical; (ii) the radicals $R_1$ and $R_2$, which may be identical or different, may also denote a residue of formula (2) below:

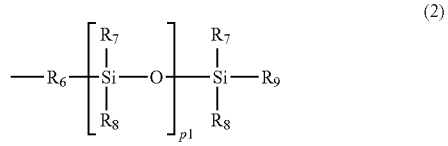

(2)

BRIEF DESCRIPTION OF THE FIGURE

FIG. 1 is a graph showing the percent increase in total UV absorbance of certain embodiments of the present invention. in which: $R_6$ is a covalent bond, a linear or branched $C_1$-$C_4$ alkyl radical or a residue of formula —$C_{m1}H_{2m1}$—O— in which $m_1$ is a number ranging from 1 to 4; $p_1$ is a number ranging from 0 to 5; the radicals $R_7$, $R_8$ and $R_9$, which may be identical or different, are each a $C_1$-$C_{18}$ alkyl radical, a $C_1$-$C_{18}$ alkoxy radical or a residue of formula (3):

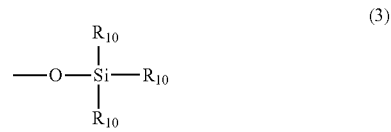

(3)

in which $R_{10}$ is a $C_1$-$C_5$ alkyl radical; $A_1$ is a residue corresponding to one of the following formulae:

(4)

(5)

(6)

in which: $R_3$ is a hydrogen atom, a $C_1$-$C_{10}$ alkyl radical, a radical of formula: —($CH_2CHR_5$—O)$_{n1}R_4$ in which $n_1$ is a number ranging from 1 to 16 or a residue of structure $CH_2$—CH—(OH)—$CH_2OT_1$ with $T_1$ having the same definition indicated above, $R_4$ is hydrogen, a metallic cation M, a $C_1$-$C_5$ alkyl radical or a residue of formula —($CH_2$)$m_2$-$OT_1$ in which $m_2$ is a number ranging from 1 to 4 and $T_1$ has the same definition indicated above, $Q_1$ is a $C_1$-$C_{18}$ alkyl radical.

In formulae (I) and (1) to (5) described above: the alkyl radicals are linear or branched and may be selected, for example, from among methyl, ethyl, n-propyl, isopropyl, n-butyl, sec-butyl, tert-butyl, amyl, isoamyl, tert-amyl, heptyl, octyl, isooctyl, nonyl, decyl, undecyl, dodecyl, tetradecyl, pentadecyl, hexadecyl, heptadecyl or octadecyl; the alkenyl radicals may be selected, for example, from among allyl, methallyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl and n-octadec-4-enyl; the alkoxy radicals are linear or branched and may be selected, for example, from among methoxy, ethoxy, n-propoxy, isopropoxy, n-butoxy, sec-butoxy, tert-butoxy, amyloxy, isoamyloxy and tert-amyloxy; the $C_1$-$C_5$ monoalkylamino or dialkylamino radicals may be selected, for example, from among methylamino, ethylamino, propylamino, n-butylamino, sec-butylamino, tert-butylamino, pentylamino, dimethylamino, diethylamino, dibutylamino and methylethylamino; the metallic cations are alkali metal, alkaline-earth metal or metallic cations selected, for example, from among lithium, potassium, sodium, calcium, magnesium, copper and zinc.

The bis-resorcinyl triazine compounds of formula (I) of the invention are screening agents that are already known per se. They are described and prepared according to the syntheses indicated in EP-A-0,775,698.

As examples of compounds of formula (I) that may be used, representative are: 2,4-bis{[4-(2-ethylhexyloxy)-2-hydroxy]phenyl}-6-(4-methoxyphenyl)-1-,3,5-triazine; 2,4-bis{[4-(3-(2-propyloxy)-2-hydroxypropyloxy)-2-hydroxy]phenyl}-6-(4-methoxyphenyl)-1,3,5-triazine; 2,4-bis{[4-(2-ethylhexyloxy)-2-hydroxy]phenyl}-6-[4-(2-methoxyethylcarboxyl) phenylamino]-1,3,5-triazine; 2,4-bis{[4-tris(trimethylsiloxysilylpmpyloxy)-2-hydroxy]phenyl}-6-(4-methoxyphenyl)-1,3,5-triazine; 2,4-bis{[4-(2″-methylpropenyloxy)-2-hydroxy]phenyl}-6-(4-methoxyphenyl)-1,3,5-triazine; 2,4-bis{[4-(1′,1′,1′,3′,5′,5′,5′-heptamethyltrisiloxy-2″-methylpropyloxy-)-2-hydroxy]phenyl}-6-(4-methoxyphenyl)-1,3,5-triazine; 2,4-bis{[4-[3-(2-propyloxy)-2-hydroxypropyloxy]-2-hydroxy]phenyl}-6-[(4-ethylcarboxyl)phenylamino]-1,3,5-triazine; 2,4-bis{[4-(2-ethylhexyloxy)-2-hydroxy]phenyl}-6-(1-methylpyrrol-2-yl)-1,-3,5-triazine.

The compounds derived from bis-resorcinyl triazine that are more particularly preferred according to the invention are selected from the group consisting of: 2,4-bis{[4-(2-ethylhexyloxy)-2-hydroxy]phenyl}-6-(4-methoxyphenyl)-1,3,5-triazine; 2,4-bis{[4-tris(trimethylsiloxysilylpmpyloxy)-2-hydroxy]phenyl}-6-(4-methoxyphenyl)-1,3,5-triazine; 2,4-bis{[4-(1′,1′,1′,3′,5′,5′,5′-heptamethyltrisiloxy-2″-methylpropyloxy-)-2-hydroxy]phenyl}-6-(4-methoxyphenyl)-1,3,5-triazine. The compound 2,4-bis{[4-(2-ethylhexyloxy)-2-hydroxy]phenyl}-6-(4-methoxyphenyl)-1,3,5-triazine or bis-ethylhexyloxyphenol Methoxyphenyl Triazine (INCI name), such as the product marketed under the trademark "Escalol S" by International Specialty Products, can be used.

According to the present invention, one or more sun-care actives can be used in combination with the bis-resorcinyl triazine compound. These actives can be selected from the group consisting of UV-A, UV-B, physical sun blockers and combinations thereof.

Example of various UV-A or UV-B sunscreens include p-aminobenzoic acid and its derivatives, anthranilates, benzophenones, camphor derivatives, cinnamic derivatives, dibenzoyl methanes, β,β-diphenylacrylate derivatives, salicylic derivatives, triazine derivatives, benzimidazole compounds, bis-benzoazolyl derivatives, methylene bis-(hydroxyphenylbenzotriazole) compounds, sunscreen polymers, silicones, and mixtures thereof.

Examples of physical sun blockers include cerium oxides, chromium oxides, cobalt oxides, iron oxides, red petrolatum, silicone-treated titanium dioxides, titanium dioxides, zinc oxides, and/or zirconium oxides and mixtures thereof.

In a preferred embodiment, the sun-care active or actives used in combination with the bis-resorcinyl triazine compound can be selected from the group consisting of p-aminobenzoic acid, oxyethylene (25 mol) p-aminobenzoate, 2-ethylhexyl p-dimethylaminobenzoate, ethyl N-oxypropylene p-aminobenzoate, glycerol p-aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4′-trimethyl ammonium)-benzyliden-bornan-2-one methylsulfate, 2-hydroxy-4-methoxybenzophenone, 2-hydroxy-4-methoxybenzophenone-5-sulfonate, 2,4-dihydroxybenzophenone, 2,2′,4, 4′-tetrahydroxybenzophenone, 2,2′-dihydroxy-4,4′dimethoxybenzophenone, 2-hydroxy-4-n-octoxybenzophenone, 2-hydroxy-4-methoxy-4′-methoxybenzophenone, beta. (2-oxoborn-3-ylidene)-tolyl-4-sulfonic acid and soluble salts thereof, 3-(4′-sulfo)benzyliden-bornan-2-one and soluble salts thereof, 3-(4′-methylbenzylidene)-d,l-camphor, 3-benzylidene-d,l-camphor, benzene 1,4-di(3-methylidene-10-camphosulfonic) acid, urocanic acid, 2,4,6-tris[p-(2′-ethylhexyl-1′-oxycarbonyl)-anilino]-1,3,5-triazine, 2-[(p-(tertiobutylamido)anilino]-4,6-bis-[(p-(2′-ethylhexyl-1′-oxycarbonyl) anilino]-1,3,5-triazine, 2,4-bis{[4-(2-ethylhexyloxy)]-2-hydroxy]-phenyl}-6-(4-methoxyphenyl)-1,3,5-triazine, N-(2 et 4)-[(2-oxohorn-3-yliden)methyl]benzyl]-acrylamide, 1,4-bisbenzimidazolyl-phenylen-3,3′,5,5′-tetrasulfonic acid, the benzalmalonate-substituted polyorganosiloxanes, the benzotriazole-substituted polyorganosiloxanes (Drometrizole Trisiloxane), dispersed 2,2′-methylene-bis-[6-(2H-benzotriazol-2-yl)-4-(1,1,3,3-tetramethylbutyl)phenol], solubilized 2,2′-methylene-bis-[6-(2H-benzotriazol-2-yl)-4-(methyl)phenol], cerium oxides, chromium oxides, cobalt oxides, iron oxides, red petrolatum, silicone-treated titanium dioxide, titanium dioxides, zinc oxides, and/or zirconium oxides and acid, salts, esters, derivatives and any combinations thereof.

The amount of the bis-resorcinyl triazine compound employed will depend on the level of protection desired. Although not to be construed as limiting, compositions will typically contain the bis-resorcinyl triazine compound in an amount of 0.1 wt. % to about 50 wt. %, preferably 0.5 wt. % to about 10 wt. % of the total weight of the composition. The amount of sunscreen agent in the composition will vary in the above range depending on the sun protection factor (SPF) desired. The higher the SPF, the greater the total amount of sunscreen agent used. Preferably, more than one sunscreen agents are included.

The term "SPF number" used in connection with the present invention refers to the dose required to produce a minimal erythema of the skin, divided by the dose required to produce the same degree of skin erythema with the product applied.

$$SPF = \frac{\text{minimal erythema dose } (MED) \text{ on protected skin}}{MED \text{ on unprotected skin}}$$

The sun-care composition of the present invention should provide the SPF value of at least 15. More preferable it should provide the SPF of at least 25 and in another preferred embodiment of the invention provides an SPF of from about 50 to about 130.

The term "copolymer" used in connection with the present invention refers to copolymers, terpolymers, tetrapolymers, etc. These acrylates/octylacrylamide copolymers are capable of enhancing the SPF value to at least 25 and more preferably from about 50 to about 130 and also forming a uniform smooth continuous film over the skin surface to provide complete protection.

The one or more sun-care active present in addition to the bis-resorcinyl triazine compound can be used in amounts from about 0.1 wt. % to about 50 wt. % of the total weight of the composition. The particular actives and amounts selected depend on the end use intended and can be readily ascertained by one skilled in the art.

The acrylates/octylacrylamide copolymer can be used from about 0.05 wt. % to about 10 wt. % of the total weight of the composition, more preferably, from about 0.5 wt. % to about 2 wt. % of the total weight of the composition.

A particularly preferred acrylates/octylacrylamide copolymer is DERMACRYL® 79 marketed by National Starch and Chemical which is a copolymer derived from N-octylacrylamide, and either acrylic acid, methacrylic acid, or simple esters thereof.

In a preferred embodiment, the acrylates/octylacrylamide copolymer can be used in combination with one or more copolymers comprising at least one vinyl pyrrolidone monomer and at least one vinyl acetate monomer present in a weight ratio from about 70:30 to about 30:70 (available from ISP under various brands PVP/VA-S-630, PVP/VA-735, PVP/VA-635, PVP/VA-535, PVP/VA-335). In another preferred embodiment, the acrylates/octylacrylamide copolymer can be used in combination with a copolymer comprising at least one vinyl caprolactam monomer and at least one vinyl acetate monomer. The copolymer comprising at least one vinyl pyrrolidone monomer and at least one vinyl caprolactam monomer can be selected from vinyl pyrrolidone/vinyl caprolactam/dimethylaminoethylmethacrylate (DMAEMA) (available from ISP under the brand name of Advantage® S, Advantage® HC-37, Advantage® LC-E), vinyl pyrrolidone/vinyl caprolactam/dimethylaminopropyl methylacrylamide (DMAPMA) (available from ISP under the brand name of Aquaflex® SF-40), vinyl pyrrolidone/vinyl caprolactam/dimethylaminopropylmethylacrylamicle (DMAPA)/methacryloylaminopropyl lauryldimonium chloride (available from ISP under the brand name of Aquastyle® 300). While the molecular weight of the vinyl acetate containing polymer is not believed to be critical, it is believed that good results can be achieved using polymers having a molecular weight from 5,000 to 100,000, and preferably from 10,000 to 65,000.

The amount of optional vinyl acetate containing copolymer in the present invention preferably ranges from about 0.05 wt. % to about 10 wt. % of the total weight of the composition. More preferably it may range from about 0.5 wt. % to about 2 wt. % of the total weight of the composition.

Examples of pharmaceutically/cosmetically/dermatologically acceptable vehicles include a cream, a lotion, an emulsion, an oil, a spray, a gel, a aerosol, an aqueous or hydra-alcoholic solution, a suspension, an anhydrous solution, a powder, a serum, an ointment, a gel, or a paste.

The amount of cosmetically acceptable vehicle in the present composition will vary considerably based upon product form, but typically will range from about 30 wt % to about 99.95 wt % and preferably about 50 wt % to about 99 wt %, based upon the total weight of the composition.

In a preferred embodiment, the sun-care composition further comprises one or more additional components selected from the group consisting of skin-feel additives, moisturizing agents film former/waterproofing agents, pH adjuster/chelating agents, emulsifiers, preservatives, anti-aging agents, skin whitening agents, exfoliating agents, treatment ingredients, fragrances and mixtures thereof.

The composition can be made into any suitable product form. Such product forms include, but are not limited to, an aerosol, balm, cream, gel, lotion, mousse, patch, pomade, pump spray, roll-on, solution, stick or towelette.

In a preferred embodiment, the present composition may be formulated in the form of an emulsion. The emulsion may be, for example, anhydrous, an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous gel, an aqueous gel, an alcoholic solutions or a hydro-alcoholic solution.

The sunscreen compositions may be prepared by using techniques and methods well known in the art. In general, ingredients are incorporated by mixing and applying heat if necessary, until the composition is uniform and homogeneous. The composition may be homogenized to ensure homogeneity and to build the proper viscosity. The sunscreen compositions of the present invention are then packaged in any package or container suitable for a sunscreen composition.

In another preferred embodiment of the present invention, there is provided a method for enhancing the SPF-value of one or more sun-care agents in UV-photoprotecting sun-care compositions comprising admixing and intimately formulating the pharmaceutically/cosmetically/dermatologically acceptable carrier and an acrylates/octylacrylamide copolymer in an amount effective to enhance the SPF value of said sun-care actives.

The sunscreen composition of the present invention is uniquely formulated to provide an enhanced feeling of softness and silkiness when the sunscreen composition is applied to the skin. Moreover, the composition is capable of being easily and uniformly applied over the skin.

The following examples further illustrate the invention.

EXAMPLES

Example 1

| Ingredients | Comp. Ex. A % W/W | Comp. Ex. B % W/W | Invention % W/W | Supplier |
|---|---|---|---|---|
| Alcohol | 71.50% | 71.50% | 71.50% | |
| Escalol 517 (Avobenzone) | 2.00% | 2.00% | 2.00% | ISP |
| Homosalate | 7.00% | 7.00% | 7.00% | Symrise |
| Escalol 587 (Octisalate) | 5.00% | 5.00% | 5.00% | ISP |
| Escalol 557 (Oxtinoxate) | 7.50% | 7.50% | 7.50% | ISP |
| Escalol 567 (Benzophenone-3) | 3.00% | 3.00% | 3.00% | ISP |
| Escalol S (Bis-Ethylhexyloxyphenol Methoxyphenyl Triazine) | 3.00% | 3.00% | 3.00% | ISP |
| Dermacryl 79 | | | 1.00% | National Starch |
| PVP/VA S630 | 1.00% | | | ISP |
| Advantage S | | 0.50% | | ISP |
| Aquaflex SF 40 | | 0.50% | | ISP |
| Total | 100.00% | 100.00% | 100.00% | |

Results of Boosting Data

| | | | | UVA | UV | Boost from control |
|---|---|---|---|---|---|---|
| Comp. Ex. C | alcohol | 77-1/3% Escalol S | no polymer | 1.209102 | 1.78119 | 0.00% |
| Comp. Ex. A | alcohol | 77-1/3% Escalol S | 1% S630 | 1.148331 | 1.824134 | 2.41% |
| Example 1 | alcohol | 77-1/3% Escalol S | 1% Dermacryl 79 | 1.672367 | 2.48941 | 39.76% |
| Comp. Ex. B | alcohol | 77-1/3% Escalol S | * | 1.498685 | 2.382909 | 33.78% |

Example 1 of this invention demonstrates that an acrylates/octylacrylamide copolymer boosted the SPF of a bis-resorcinyl triazine containing sunscreen composition even better than other commercially available film forming polymers known to significantly increase SPF.

While the invention has been described in detail with respect to preferred embodiments thereof featuring an acrylates/octylacrylamide copolymer in combination with a bis-resorcinyl triazine, it is believed that it can be practiced in conjunction with analogous acrylates copolymers such as Dermacryl® C, Dermacryl® AQF and Dermacryl® LT in combination with bis-resorcinyl triazines.

The invention has been described in detail with particular reference to preferred embodiments thereof, but it will be understood that variations and modifications can be effected within the spirit and scope of the invention.

We claim:

1. A sun-care composition having an SPF value of at least 25 comprising:
   (a) one or more sun care actives including bis-ethylhexyl-oxyphenol methoxyphenyl triazine;
   (b) an acrylates/octylacrylamide copolymer;
   (c) a pharmaceutically/cosmetically/dermatologically acceptable vehicle; and
   (d) a copolymer selected from the group consisting of a vinyl pyrrolidone/vinyl caprolactam/dimethylaminopropyl methylacrylamide copolymer, a vinyl pyrrolidone/vinyl caprolactam/dimethylaminopropylmethylacrylamide/methacryloylaminopropyl lauryldimonium chloride copolymer, and mixtures thereof.

2. The composition according to claim 1, further comprising a second sun-care active selected from the group consisting of UV-A, UV-B, physical sun blockers and combinations thereof.

3. The composition according to claim 2, wherein the UV-A, UV-B or physical sun blocker is selected from the group consisting of p-aminobenzoic acid, oxyethylene p-aminobenzoate, 2-ethylhexyl p-dimethylaminobenzoate, ethyl N-oxypropylene p-aminobenzoate, glycerol p-aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammonium)-benzyliden-boman-2-one methyl sulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4'dimethoxybenzophenone, 2-hydroxy-4-n-octoxybenzophenone, 2-hydroxy-4-methoxy-4'-methoxybenzophenone, β (2-oxoborn-3-ylidene)-tolyl-4-sulfonic acid, 3-(4'-sulfo)benzyliden-bornan-2-one and soluble salts thereof, 3-(4'methylbenzylidene)-d,l-camphor, 3-benzylidene-d,l-camphor, benzene 1,4-di(3-methylidene-10-camphosulfonic) acid, urocanic acid, 2,4,6-tris[p-(2'-ethylhexyl-1'-oxycarbonyl)-anilino]-1,3,5-triazine, 2-[(p-(tertiobutylamido)anilino]-4,6-bis-[(p-(2'ethylhexyl-1'-oxycarbonyl)-anilino]-1,3,5-triazine, N-(2 et 4)-[(2-oxoborn-3-yliden)methyl]benzyl]-acrylamide, 1,4-bisbenzimidazolyl-phenylen-3,3',5,5'-tetrasulfonic acid, the benzalmalonate-substituted polyorganosiloxanes, benzotriazole-substituted polyorganosiloxanes (Drometrizole Trisiloxane), dispersed 2,2'-methylene-bis-[6-(2H-benzotriazol-2-yl)-4-(1,1,3,3-tetrame-thylbutyl)phenol], solubilized 2,2'-methylene-bis-[6-(2H-benzotriazol-2-yl)-4-(methyl)phenol, cerium oxides, chromium oxides, cobalt oxides, iron oxides, red petrolatum, silicone-treated titanium dioxide, titanium dioxide, zinc oxide, zirconium oxide, and acid, salts, esters, derivatives and combinations thereof.

4. The composition according to claim 1, wherein the acrylates/octylacrylamide copolymer contains more than one acrylates monomer and at least one octylacrylamide monomer.

5. The composition according to claim 1, wherein the bis-ethylhexyl-oxyphenol methoxyphenyl triazine compound is 2,4-bis{[4-(2-ethyl-hexyloxy)]-2-hydroxy]-phenyl}-6-(4-methoxyphenyl)-1,3-,5-triazine.

6. The composition according to claim 1, wherein the bis-ethylhexyl-oxyphenol methoxyphenyl triazine compound is present in an amount of about 0.1 wt. % to about 50 wt. % of the total weight of the composition.

7. The composition according to claim 1, wherein the acrylates/octylacrylamide copolymer is present in an amount of about 0.05 wt. % to about 10 wt. % of the total weight of the composition.

8. The composition according to claim 6, wherein the acrylates/octylacrylamide copolymer is present in an amount of 0.5 wt. % to about 2 wt. % of the total weight of the composition.

9. The composition according claim 1 further comprising a vinyl pyrrolidone/vinylacetate copolymer or a vinyl caprolactam/vinyl acetate copolymer present in an amount of 0.05 to 10 wt. % of the total weight of the compositions.

10. The composition according to claim 1, further comprising one or more additional components selected from the group consisting of skin-feel additives, moisturizing agents film former/waterproofing agents, pH adjuster/chelating agents, emulsifiers, preservatives, and mixtures thereof.

11. A method for enhancing the SPF-value of one or more sun-care actives including bis-ethylhexyl-oxyphenol methoxyphenyl triazine in UV-photoprotecting sun-care compositions comprising admixing the bis-ethylhexyl-oxyphenol methoxyphenyl triazine; a pharmaceutically/cosmetically/dermatologically acceptable carrier wherein the pharmaceutically/cosmetically/dermatologically acceptable carrier comprising about 70% alcohol; a copolymer selected from the group consisting of a vinyl pyrrolidone/vinyl caprolactam/dimethylaminopropyl methylacrylamide copolymer, a vinyl pyrrolidone/vinyl caprolactam/dimethylaminopropylmethylacrylamide/methacryloylaminopropyl lauryldimonium chloride copolymer, and mixtures thereof; and an acrylates/octylacrylamide copolymer in an amount effective to enhance the SPF value of said sun-care actives.

12. A sun-care composition having an SPF value of at least 25 comprising:
  (a) about 70% alcohol;
  (b) avobenzone;
  (c) octisalate;
  (d) oxtinoxate;
  (e) benzophenone-3;
  (f) bis-ethylhexyl-oxyphenol methoxyphenyl triazine;
  (g) an acrylates/octylacrylamide copolymer; and
  (h) a copolymer selected from the group consisting of: a vinyl pyrrolidone/vinyl caprolactam/dimethylaminopropyl methylacrylamide copolymer, a vinyl pyrrolidone/vinyl caprolactam/dimethylaminopropylmethylacrylamide/methacryloylaminopropyl lauryldimonium chloride copolymer, and mixtures thereof.

* * * * *